United States Patent [19]

Varga et al.

[11] Patent Number: 5,288,718
[45] Date of Patent: Feb. 22, 1994

[54] METHOD FOR DECORPORATING RADIOACTIVE ISOTOPE FROM LIVING ORGANISM

[75] Inventors: László Varga, Budapest; Mihály Törőcsik, Tószeg; László B. Sztanyik, Budapest; Erno Brücher, Debrecen; József Emri, Debrecen; Béla Győri, Debrecen, all of Hungary

[73] Assignees: Országos "Frederic Joliot-Curie" Sugárbiológiai és Sugáregészségügyi Kutató Intézet, Budapest; Agromen Agrármenedzseri Kft, Szolnok; Magyar Külkereskedelmi Bank Rt., Budapest, all of Hungary

[21] Appl. No.: 80,985

[22] Filed: Jun. 21, 1993

Related U.S. Application Data

[63] Continuation of Ser. No. 646,762, Jan. 17, 1991, abandoned.

[30] Foreign Application Priority Data

May 24, 1989 [HU] Hungary ................ 2614/89

[51] Int. Cl.$^5$ ............ A61K 31/33; A61K 49/02
[52] U.S. Cl. .................... 514/183; 514/184; 424/10; 424/1.81; 540/467; 540/470
[58] Field of Search ............ 514/183, 184; 424/10; 540/467, 470

[56] References Cited

U.S. PATENT DOCUMENTS 4,687,844  8/1987  Gokel et al. ............ 540/467

FOREIGN PATENT DOCUMENTS 2024822A  1/1980  United Kingdom .

OTHER PUBLICATIONS

J. Batsch et al., Removal os Strontium-85, etc., Nukieonika, vol. 23, p. 305 (1978).
C. A. Chang, Metal Complex Formation, Inorg. Chem. vol. 22, p. 3866 (1983).
A. Catsch et al., Radioactive Metal Mobilization in Medicine, Charles C. Thomas, Publ., (1964).
G. A. Melson (Ed.) (Lamb et al.) Coordination Chemistry of Macrocyclic Compounds, Plenum Press, pp. 145-217 (1979).
W. H. Müller et al., Enhanced $^{224}$Ra/$^{212}$Pb Excretion, etc., Naturwiss, vol. 61 p. 455, (1974).
W. H. Müller, SR-85 Decorporation With A Cryptating Agent, vol. 57, p. 248 (1970).
W. H. Müller, $^{140}$Ba/$^{140}$La Excretion, etc., Naturwiss., vol. 64, pp. 96-97 (1977).
Blasius et al. Chem. Abs. vol. (101) #237067u, 1984.
Kozlov et al. Chem. Abs. vol. (96) #224118q, 1982.
F. deJong et al., J. Royal Netherlands Chemical Society, 102(3), 164-173, 1983.

*Primary Examiner*—John M. Ford
*Assistant Examiner*—Y. N. Gupta
*Attorney, Agent, or Firm*—Schweitzer Cornman & Gross

[57] ABSTRACT

Pharmaceutical composition for decorporating radioactive isotopes from living organisms comprising as active agent a product prepared by reacting 1,4,10,17-tetraoxa-7,16-diazacyclooctadecane with 2-bromomalonic acid disodium salt.

6 Claims, 6 Drawing Sheets

METHOD FOR DECORPORATING RADIOACTIVE ISOTOPE FROM LIVING ORGANISM

This is a continuing application of U.S. Ser. No. 646,762, filed on Jan. 17, 1991, now abandoned.

This invention relates the preparation of active ingredients and pharmaceutical compositions for decorporating radioactive isotopes from living organisms.

Nuclear fissions in the experimental, isotope-producing, or energy-supplying nuclear reactors and in nuclear weapon tests are accompanied by the formation of a considerable amount of radioactive by-products. Majority of these hot materials involves fission products and activated elements, including extremely hazardous radioactive isotopes such as iodine-131, strontium-89-90, cesium-134 and -137, cerium-141 and -144. Emitted into the environment, they may result in a radioactive pollution to the kingdom of life.

There are three ways, three gates, these isotopes can get through entering the human body: the respiratory tract (breathing with air), the digestive tract (ingesting with foods and drinks), the epiderm (contacting with harmed or unharmed skin).

A good deal of possibilities are provided for reducing or even preventing injuries of health. Some isotopes, essentially radiostroncium, however, can only be protected from by hindering its gastrointestinal resorption with peroral administration of suitable adsorbents. If the medical aid begins as late as several hours after the contamination, no efficient methods are available at the present state of the medical art for the resorbed proportion of the radioisotopes transported by the blood-stream and the lymph-flow to influence their deposition in bones, to prevent their histic binding and to promote their decorporating.

This fact motivates the research on highly effective human and veterinary pharmaceuticals capable of bonding radiostrontium in the blood-stream and in other extracellular regions in form of stable complexes. This would prevent the histic deposition of the isotope and permit its natural excretion (faeces, urine) from the organism.

The following requirements are established to such a pharmaceutical agent:

(a) the complex formation takes place in the biological system even in the presence of concurrent ions (such as $Ca^{2+}$, $Na^+$, $K^+$, etc.) and ligands that are present in a great amount;
(b) it has an acceptably low level of toxicity (wide-range efficiency);
(c) it is water-soluble; and
(d) it can be administered parenterally as well.

In the early fifties when the rapid development of coordination chemistry commenced, predominantly the transition metal complexes were studied, overshadowing the alkali and alkali earth metal ones that either do not form complexes with the readily accessible organic and inorganic ligands or these complexes have very low stability, only electrostatic inter-relations between the metal ions and the ligands keep them together. This concept was broken through by the discovery of "crown ether" and "cryptate" ligands in the late sixties.

Crown ethers contain mainly oxygen donor atoms while cryptates have both oxygen and nitrogen donors. Their construction holds the incorporated metal ions in cavities of well-defined size thus, only metals of certain sizes can form stable complexes with these types of ligands. Consequently, they are much more specific than ligands known before. Stability constants (log K) for some of these ligands with alkali earth metals in aqueous solution are presented in Table I (Coordination Chemistry of Macrocyclic Compounds, Ed. G. A. Melson, Plenum Press, 1979).

TABLE I

| Ligand | $Ca^{2+}$ | $Sr^{2+}$ | $Ba^{2+}$ |
|---|---|---|---|
| 15-crown-5 | 0.5 | 2.72 | 3.87 |
| dicyclohexyl-18-crown-6 | 0.4 | 2.64 | 3.27 |
| dibenzo-18-crown-6 | — | 1.00 | 1.95 |
| 1,10-diaza-4,7,13,16-tetra-oxycyclo-octadecane | — | 2.56 | 2.97 |
| cryptate-(2.1.1) | 2.50 | 2.00 | 2.00 |
| cryptate-(2.2.1) | 6.95 | 7.35 | 6.30 |
| cryptate-(2.2.2) | 4.40 | 8.00 | 9.50 |
| cryptate-(3.2.2) | 2.00 | 3.40 | 6.00 |
| cryptate-(3.3.2) | 2.00 | 2.00 | 3.65 |

Date in Table I show a very considerable effect of the size of ligand "cavity" on the stability constants. In some cases, such as for cryptate-(2.2.2), the stability constant with $Sr^{2+}$ is higher by several orders of magnitude than with $Ca^{2+}$.

The above data motivated animal tests with the ligand cryptate-(2.2.2) (4,7,13,16,21,24-hexaoxa-1,10-diazabicyclo-/8.8.8/-hexacosane) for removal of Sr-85, Ra-224, Pb-212, and Ba-140 as well as La-140 isotopes from the organisms (W. H. Müller, Naturwiss. 57, 248/1970/; W. H. Müller and W. A. Müller, Naturwiss. 61, 455/1974/; W. H. Müller et al., Naturwiss. 64, 96/1977/; J. Knajfl et al., 12th Ann. Meeting of ESRB, Budapest, 1976; J. Barsch, J. Geisler and Z. Szot, Nukleonika 23, 305/1978/). The value of their result was vitiated by the concept that the metal complexes were formed in vitro then administered subcutaneously and their purging was studied. These experiments could prove only the fact that no dissociation of the complex formed externally from the radioactive metal and the ligand occured in an intricate biological system instead of an in vivo complexation of the radioactive isotope existing already in the animal with the ligand administered subsequently into a stable complex which could be decorporated from the organism in the natural ways of excretion. It should be noted on the basis of real experiences that ligand compounds are much less toxic in complex form than the ligands themselves.

In contrast to known complexes, stability constants of rare earth metal complexes of 1,10-diaza-4,7,13,16-tetraoxacyclooctadecane-N,N'-diacetic acid, synthesized from the monocyclic cryptate decrease with the increasing atomic number (decreasing ionic size). Stability constants of $Ca^{2+}$ and $Sr^{2+}$ complexes, however, are identical within the experimental error (8.39 and 8.29, respectively) (C. A. Chang and M. E. Rowland, Inorg. Chem. 22, 3866 (1983)) while complexes of non-cyclic aminopolycarboxylic acids (EDTA, ethylenediaminetetraacetic acid, DTPA, diethylenetriaminepent-acetic acid, etc.) are considerably more stable with $Ca^{2+}$ than with $Sr^{2+}$.

The purpose of this invention was the preparation of monocyclic cryptate ligands and their derivatives in order to influence in vivo stabilities of complexes favourably by linking functional groups to the macrocycles. The final goal was to attain derivatives that would be suitable for the removal of radiostrontium, occasionally other radioactive metal isotopes, from the living organisms. It was proved by several experimental data that an active agent based on 1,4,10,13-tetraoxa-7,16-diazacyclooctadecane-N,N'-dimalonic acid tetrasodium salt was capable of promoting the excretion of radiostroncium and radiocerium which had been administered into various sites (peritoneal cavity, subcutaneous interstitial tissue, lung) of the animal body.

The method of this invention comprises a new method to the preparation of compositions containing 1,4,10,13-tetraoxa-7,10-diazacyclooctadecane dimalonic salts.

Preparation of such a compound was described by F. de Jong et al. (Recl. Trav. Chim. Pays-Bas, 102, 164–173/1983/). In this procedure, 1,4,10,13-tetraoxa-7,10-diazacyclooctadecane was reacted with alpha-halogenated methyl malonate ester for substituting hydrogen atoms on the nitrogen atoms and then ester was hydrolyzed into lithium salt.

We have found that alpha-brominated disodium malonate is more preferable for substituting hydrogen atoms on the nitrogen atoms than alpha-halogenated methyl malonate. In this case, hydrolysis is omitted and the water-soluble salt is obtained directly. In addition, sodium salt is not hygroscopic in contrast to lithium salt thus, it is a more convenient active ingredient for the preparation of pharmaceutical compositions or the like. Another advantage of sodium salt to lithium one is its lower price.

In the procedure of this invention, the active agent containing 1,4,10,13-tetraoxa-7,16-diazacyclooctadecane-N,N'-dimalonic acid tetrasodium salt is prepared by reacting 1,4,10,13-tetraoxy-7,16-diazacyclooctadecane with 2-bromomalonic acid disodium salt. Preferably, the reaction is carried out in a slightly alkalic aqueous medium at 70° to 80° C. Alkalicity of the reaction mixture is reasonably checked with phenolphthalein indicator, adjusting and holding a pale pink colour of the mixture during the reaction.

The active agent containing 1,4,10,13-tetraoxy-7,16-diazacyclooctadecane-N,N'-dimalonic acid tetrasodium salt is capable of bonding radioactive metal isotopes, principally radiostroncium and radiocerium, ingested into a living organism. The stable complex formed in vivo can be decorporated from the body in the natural ways in form of this complex.

The pharmaceutical composition of this invention comprises an active ingredient containing 1,4,10,13-tetraoxa-7,16-diazacyclooctadecane-N,N'-dimalonic acid tetrasodium salt prepared by the procedure of this invention along with a pharmaceutically accepted carrier, such as normal saline solution or a 5-per cent by volume of glucose solution.

The composition comprises from 100 to 500 mg, preferably 250 mg of active ingredient mixed preferably with a 5-per cent by volume of glucose solution.

Healing power of the composition has been evidenced by animal tests. In this way, the minimum and average lethal doses ($LD_{0.1}$ and $LD_{50}$, respectively) have been established.

For the determination of lethal doses, the active ingredient was administered intravenously at increasing concentrations to the animals. Minimum and average lethal doses were calculated from the mortality within 30 days. $LD_{50/30}$ value of the active agent containing 1,4,10,13-tetraoxa-7,16-diazacyclooctadecane-N,N'-dimalonic acid tetrasodium (DMCRYP) salt×NaBr (x=2.5–8) as prepared according to Example I was 1.05 mmole/kg body weight. On every occasion, one tenth of this dose was introduced into each animal in this experiment.

Laboratory Small Animal Tests for the Effect of DMCRYP on the Enhanced Decorporation The pharmaceutical composition containing DMCRYP active ingredient was denoted "PTR-23". The composition contained a carrier, preferably sterilized normal saline solution or 5-per cent by weight of glucose solution. Preferable ratio of active agent to carrier was from 100 to 500 mg/cm$^3$ carrier.

In order to test the effect of DMCRYP on enhancing the decorporation of radiostroncium and the rare earth metal radiocerium from the body, male and female Swiss mice and Wistar rats were selected. The experiments were generally conducted by administration of radiostroncium ($^{85}SrCl_2$) or radiocerium ($^{144}CeCl_3$) of an activity from 37 to 54 kBq (1–2 μCi) into various sites of the animal body (peritoneal cavity, subcutaneous interstitial tissue, lung) followed by an intravenous injection of PTR-23 30 to 60 minutes later so that one injection introduced 100 μmole/kg of active agent. In the comparative tests, a known polyaminopolycarboxylic acid-type decorporant (decorporating agent), calcium-trisodium salt of DTPA (diethylenetriaminopentacetic acid) (Heyl and Co., Berlin) was used at equimolar concentration. The amount of residual isotopes in the animal organisms was determined by whole-body activity measurements in every 1 to 4 days and was expressed as per cent of activity introduced.

Figure 1:
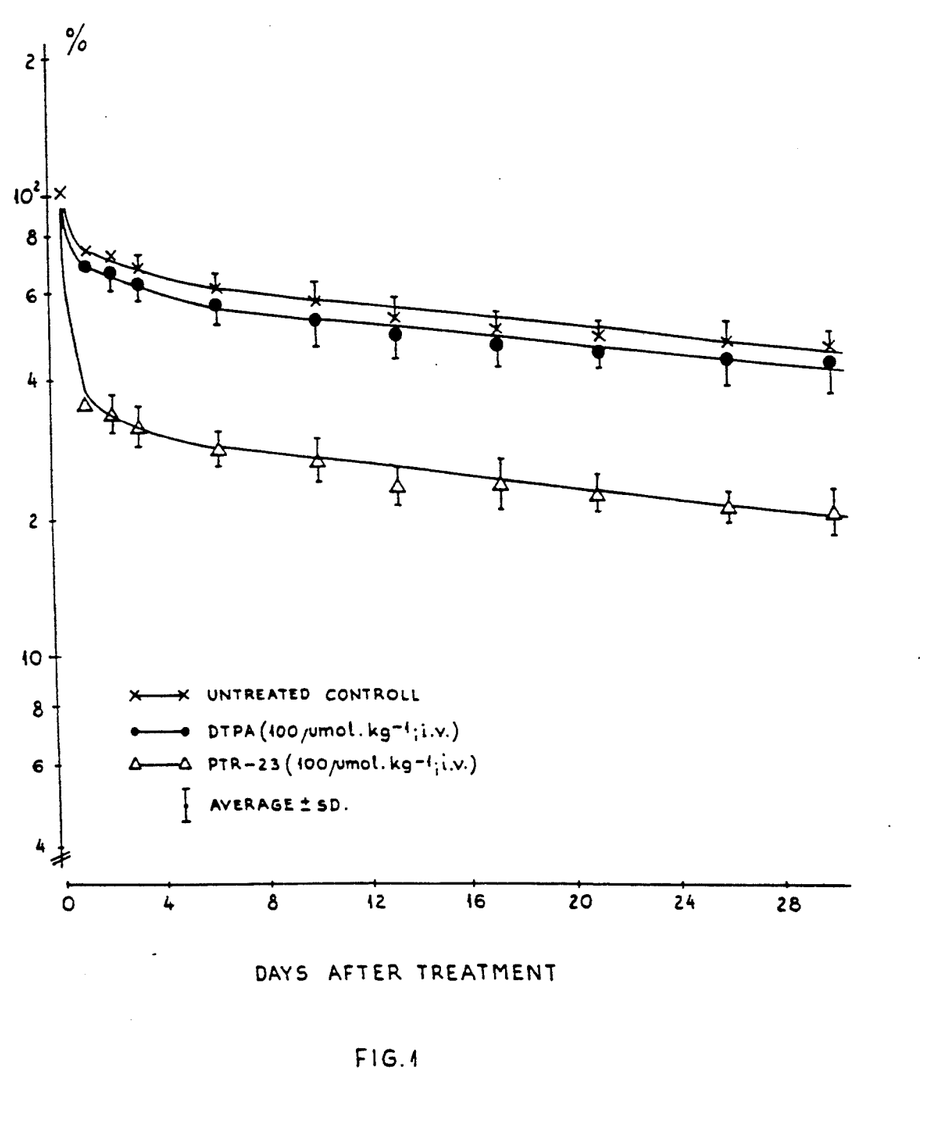
Figure 2:
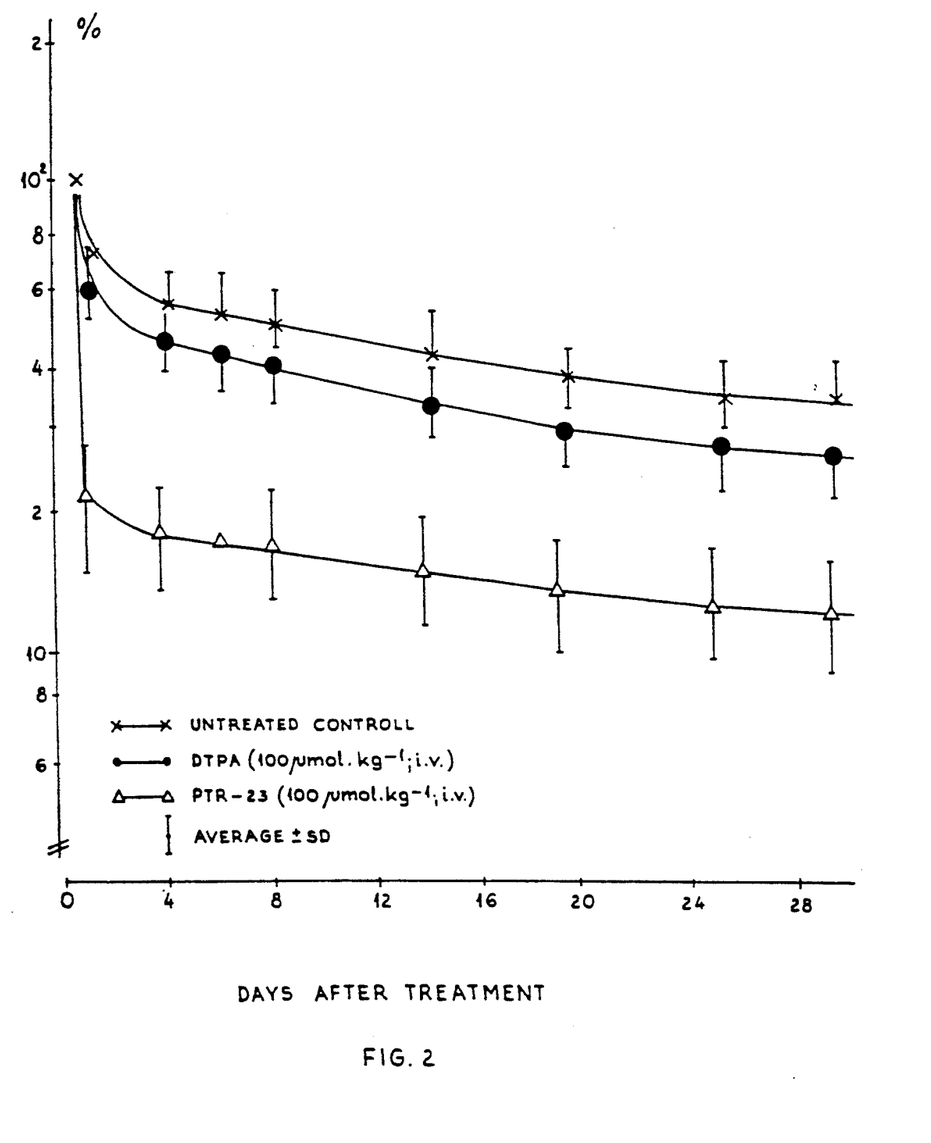
Figure 3:
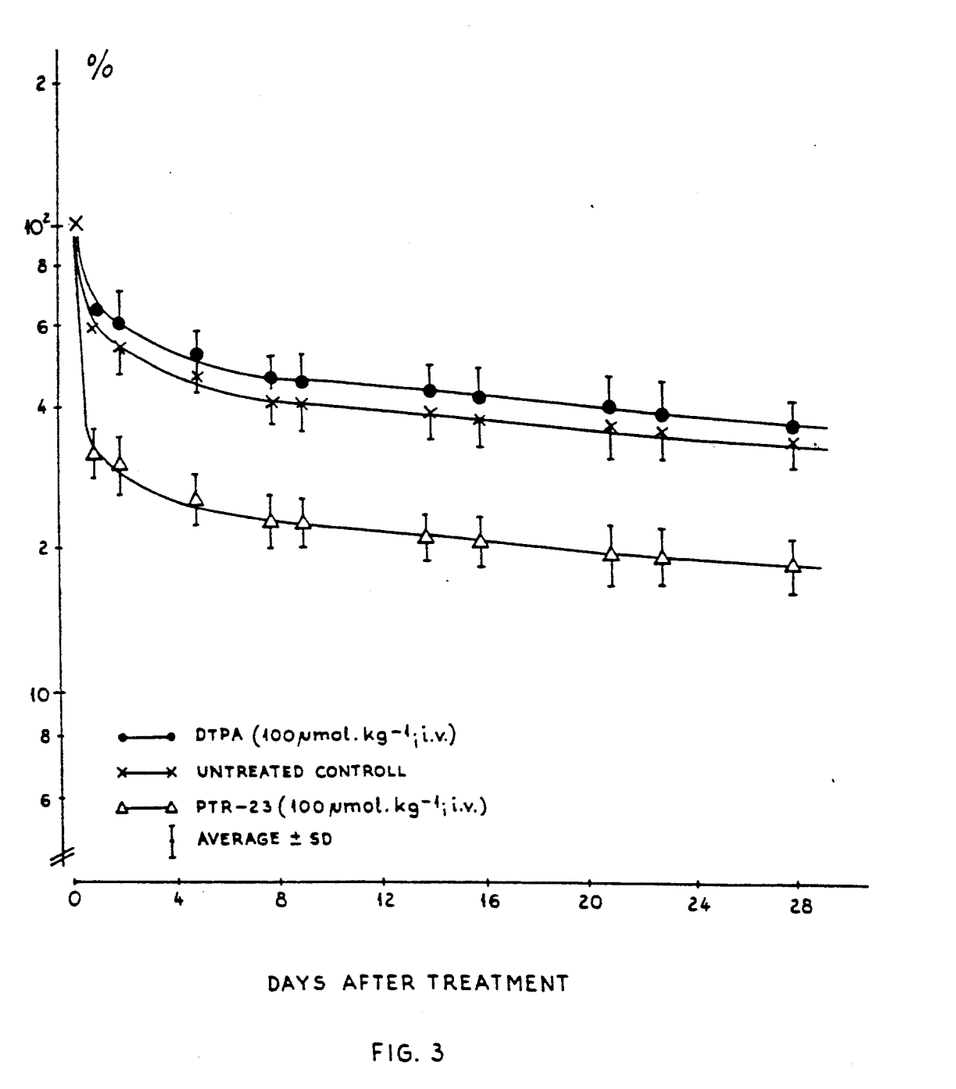

DESCRIPTION OF FIGS. 1-2-3

The effect of PTR-23 administered once (Day 0) intravenously on the enhanced excretion of Sr-85 isotope introduced into the peritoneal cavity is illustrated in FIG. 1 where the percentage of residual isotopes in the animal body (whole-body retention) is plotted against the days of experiment. The efficiency of treatment with the compound of this invention 30 minutes after the administration of the isotope is indicated by the steep drop of the corresponding curve: on the Day 1, 35.8 per cent was attained which is less than a half of the Sr-85 content of control animals being 73.2 per cent. This ratio was consistent throughout the experiment, reaching 21.2 per cent after the treatment with PTR-23 in contrast to the 45.5 per cent of untreated controls. This series of experiments also illustrates that the decorporant DTPA is ineffective for removal of Sr isotope from the animal body (A. Catsch: Dekorporierung radioaktiver und stabilier Metallionen, K. Thiemig Verlag, München, 1968).

The present invention is more particularly illustrated by the following examples which are not intended to limit the scope of the invention.

Example 1 demonstrates the preparation of the active agent. Examples 2 through 6 illustrate the healing power of pharmaceutical compositions prepared therefrom.

EXAMPLE 1

Preparation of 1,4,10,13-tetraoxa-7,16-diazacyclooctadecane-N,N'-dimalonic acid tetrasodium salt (DMCRYP)-Containing Active Agent 2.80 g (15.3 mmole) of 2-bromomalonic acid was dissolved in 2 cm$^3$ of water and the solution was titrated with 1.5 to 2M NaOH solution in the presence of 1 drop of phenolphthalein indicator to a pale pink colour. 1.00 g (3.81 mmole) of 1,4,10,13-tetraoxy-7,16-diazacyclooctadecane (Kryptofix 22, Merck) was added to the solution. The reaction mixture was kept at 75° to 80° C. for 14 hours while 8.55 cm$^3$ of 1.873M NaOH solution was dropped from a buret for maintaining the pink colour. The solution was then evaporated in vacuo and dehydrated still in vacuo on a water-bath at 80° C. for 6 hours. The residue was taken up with 15 cm$^3$ of dichlormethane, filtrated, extracted three times with dichlormethane and dried in nitrogen stream. The white solid product was extracted with absolute ethanol until no considerable amount of material had been dissolved (15 to 17 times). A white deposit was precipitated from the extract during the extraction. The ethanolic extract was evaporated, taken up with dichlormethane, filtered, extracted three times with dichlormethane and dried in nitrogen stream. Yield of the product was 1.447 g.

The dichlormethane extract was evaporated in nitrogen stream and 0.357 g of highly hygroscopic yellowish crystals were obtained.

The residue from ethanolic extraction (said white precipitate) was dissolved in 20 cm$^3$ of water and kept at 80° C. for 20 minutes. The solution was evaporated in vacuo and dehydrated still in vacuo on a water-bath at 80° C. for 5 hours. The further processing was the same as above. The ethanolic extract was evaporated in vacuo, taken up with dichlormethane, filtered, and dried in nitrogen stream. 0.430 g solid was obtained.

Products from ethanolic extracts were combined, suspended in ethanol and stirred at 70° C. for 30 minutes. The mixture was then evaporated, taken up with dichlormethane, filtered, and dried in nitrogen stream. Mass of the product was 1.830 g at a yield of 58 per cent. The product is a double salt of 1,4,10,13-tetraoxa-7,16-diazacyclooctadecane-N,N'-dimalonic acid tetrasodium salt with sodium bromide (containing 33% by weight sodium bromide).

Analysis:
Characteristic IR bands (in KBr), cm$^{-1}$: 2950, 2868 (m, $\nu$/C—H/); 1605 (vs, $\nu$/COO/$_{as}$); 1430 (m, $\nu$/COO$_s$).

Characteristic unidentified IR bands: 1350 (s), 1320 (s), 1905 (s); 928 (w).

$^1$H NMR data (in D$_2$O), ppm: 2.92 (t, 8H, N—CH$_2$); 3.63 (t, 8H, O—CH$_2$); 3.70 (sg, 8H, O—CH$_2$—CH$_2$—O); 4.00 (sg, 2H, N—CH).

Water solubility: very soluble.

EXAMPLE 2

The results with female Wistar rats are shown in FIG. 2. The experimental arrangement and notations are identical to those in the general description and in FIG. 1. The only difference was in the delay between the introduction of the isotope into the peritoneal cavity and the intravenous administration of the active agent, being 60 days. The composition of this invention was even more efficient for rats. On the first day after the treatment, the amount of radiostroncium in the animal bodies dropped to 22.0 percent by virtue of the new complexing agent as compared to the 69.6 percent with the control which is more than three times higher. Like the results with mice, the ratio between the curves was consistent throughout the experiment reaching 13.5 and 36.8 percent of residue at the end of test for the treated and the control animals, respectively. Retention values in the DTPA-treated group were lower than those in the control but the difference was not statistically significant.

It was clearly demonstrated by the experimental data in Example 2 that the composition PTR-23 promoted the decorporation of Sr-85 administered into the peritoneal cavity considerably, reducing thereby the radioactive load of the animal organism exposed to a single relatively low dose when the agent had been ingested into the blood-stream 60 minutes after the administration of the isotope.

EXAMPLE 3

In this series of experiments, possibilities of decorporating radiostroncium got into the skin or the subcutaneous interstitial tissues were studied with a single intravenous treatment by PTR-23 (FIG. 3).

The results demonstrated that the amount of radiostroncium entered through the hurt epiderm (stabs, bruises, cuts) was markedly decreased by the composition PTR-23. Whole-body retention of the animals was 31.5 percent in contrast to 56.9 percent of the control (a gain of almost 50 percent) on the Day 1 when the treatment was applied 30 minutes after the infection. This ratio was consistent throughout the experiment. Treatment with DTPA was ineffective again.

Figure 4:
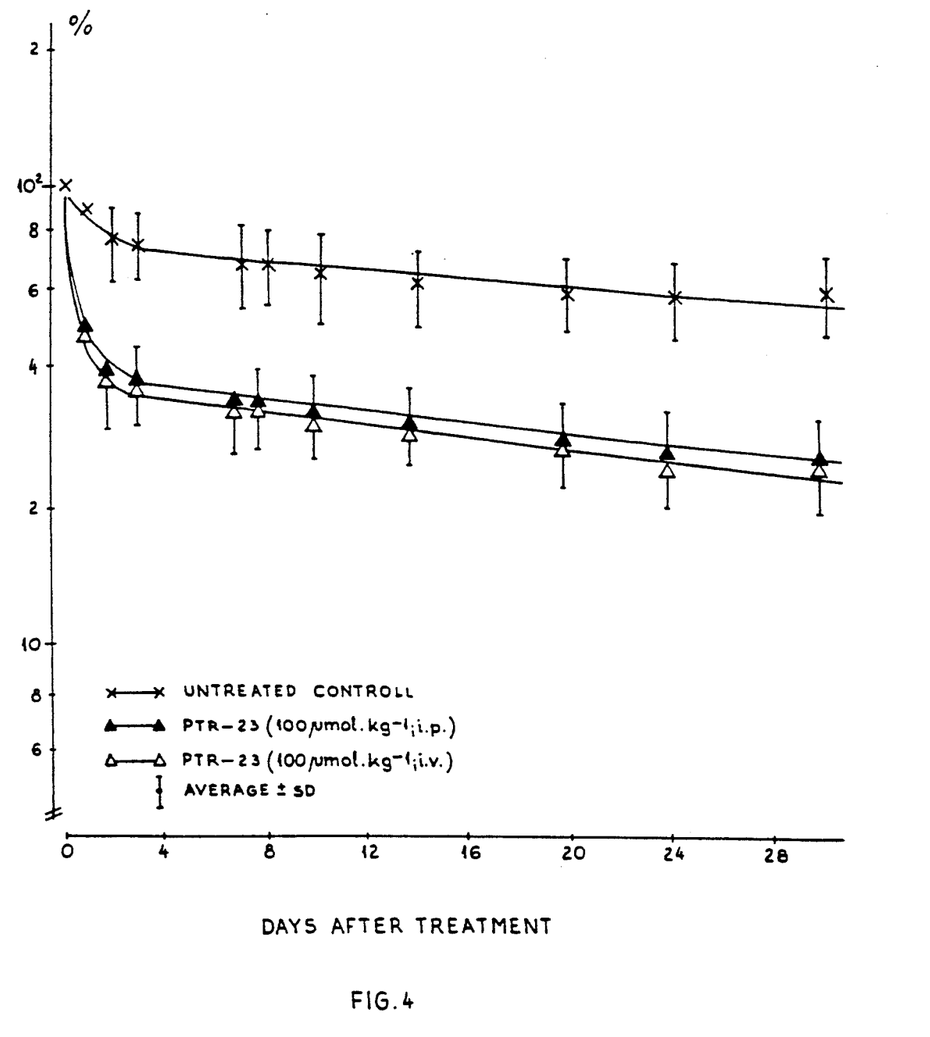

DESCRIPTION OF FIG. 4

EXAMPLE 4

Whole-body retention curves in FIG. 4 refer to the elimination of radiostroncium ingested through the trachea into the lungs of Wistar rats after the administration of the composition PTR-23 intravenously or intraperitoneally. It was proved unequivocally by the experimental data that the efficiency of the agent was not influenced by the way of administration, i.e. identical effect was obtained both with intravenous and with intraperitoneal treatment.

The effect of the composition of this invention on the promotion of Sr decorporation is shown by the two lower curves in FIG. 4. It can be seen again that the amount of Sr isotope ingested into the lungs decreased abruptly after the administration of the said composition. On the Day 1, it dropped to 48.2 percent while this level was 88.3 percent in the control. The highest difference was obtained on the Day 18 when the retentions in the treated and control groups were 28.6 and 58.7 percent, respectively.

Figure 5:
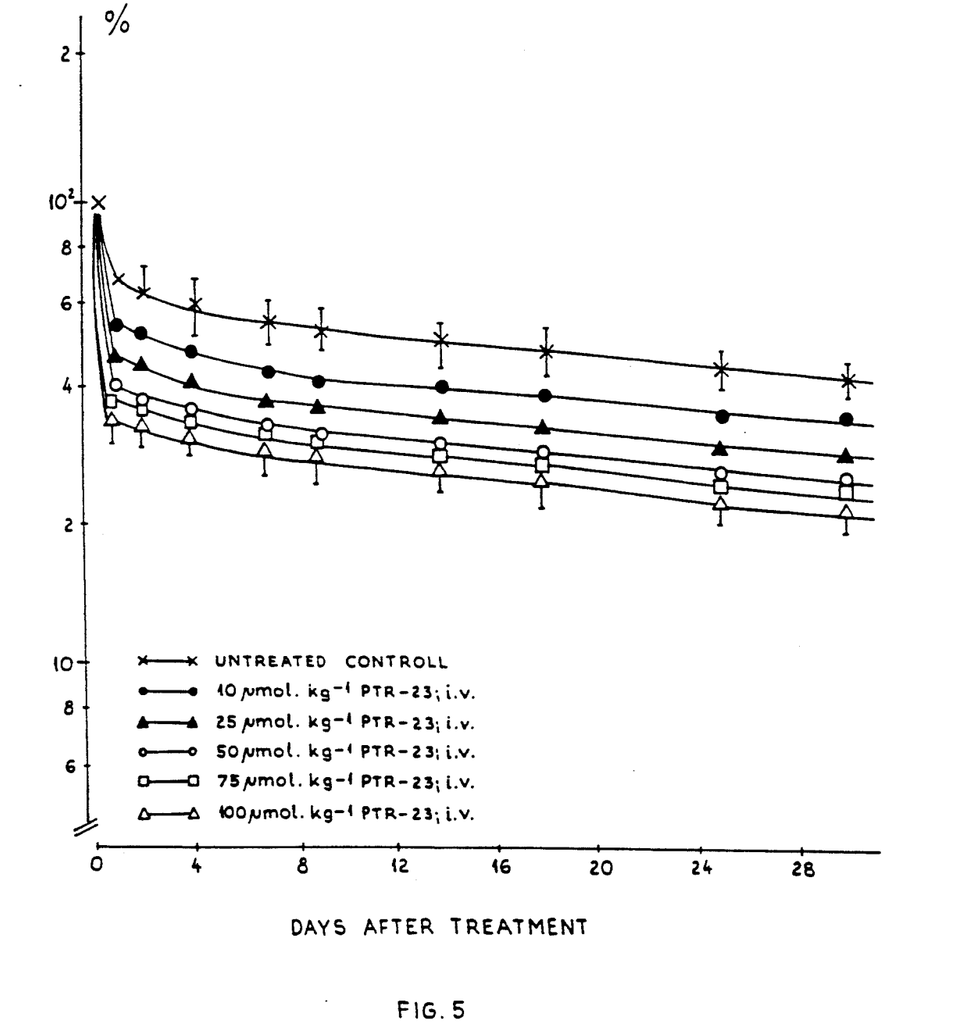

DESCRIPTION OF FIG. 5

EXAMPLE 5

The dose effect of the decorporant of this invention was measured on Swiss mice. Retention curves in FIG. 5 represent an order of magnitude in the concentration of the agent (from 10 to 100 $\mu$mole/kg) following the excretion of Sr isotope ingested peritoneally. It was established from the experimental data that, at a concentration of as low as 10 $\mu$mole/kg, the amount of isotope retained in the body was significantly lower than that in the control. The effect increased with the dose but above 50 $\mu$mole/kg, the enhancement in the excretion was not proportional to the amount of the active agent as shown by retention values at the end of experiments (Day 30) being 40.6 percent in the control and 34.3, 28.3, 25.2, 23.9 and 21.8 percent in the order of increasing dose. Consequently, it seemed to be reasonable to administer lower doses repeatedly for treating an internal infection of radiostroncium.

Figure 6:
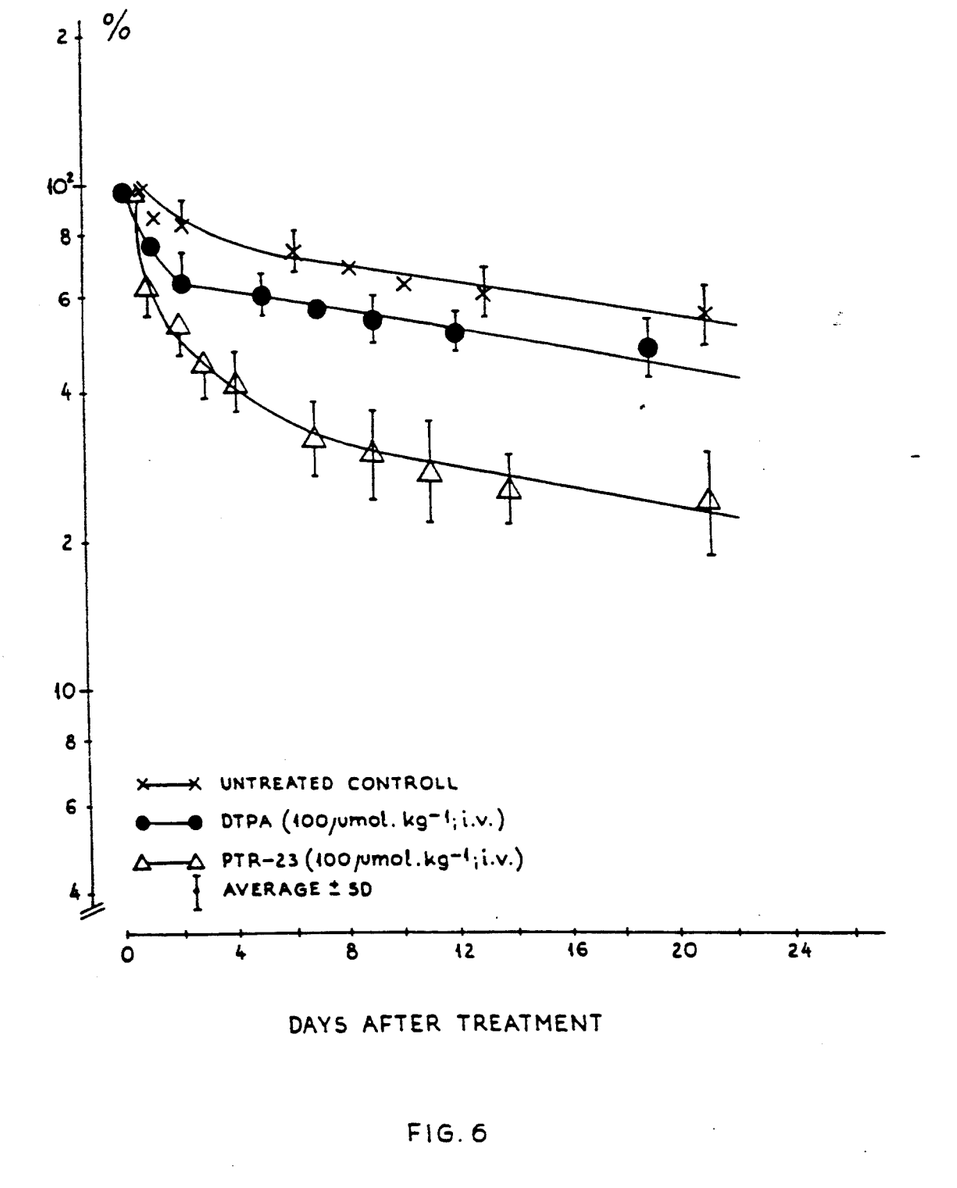

DESCRIPTION OF FIG. 6

EXAMPLE 6

The pharmaceutical composition of this invention was tested to other radioactive metals than radiostroncium, mainly to the rare earth metal, cerium-144 for its removal from the animal body. Cerium-144 isotope was introduced peritoneally into female Swiss mice. 30 minutes after, the animals were treated intravenously with 100 μmole/kg of PTR-23 or DTPA. Treatments were repeated twice, on the Days 2 and 4. The results are shown in FIG. 6. Whole-body retention curves characteristic to excretion of the isotope revealed that decorporating of the active isotope from the animals was relatively slow in the control group. The first treatment with DTPA caused a slight decrease in the retention on the Day 2 (72.8 percent as compared to 85.9 percent) but the second and third treatments were ineffective, i.e. the further course of the two curves were identical. On the contrary, after the administration of the composition of this invention, the activity retained in the body was only 56.2 percent on the Day 2 (at the moment of the second treatment) in contrast to the above rate of 85.9 percent. The difference was increasing due to the second and third treatments until the Day 7 when the level in the PTR-23 group was 33.4 per cent while the control level was 76.3 percent (i.e. nearly two and a half-fold of the former). From this time, the rates of excretion (decorporation) were identical thus, the course of the curves was parallel.

It was unequivocally demonstrated by the Examples that the composition containing 1,4,10,13-tetraoxa-7,16-diazacyclooctadecane-N,N'-dimalonic acid tetrasodium salt (DMCRYP) (PTR-23) a favourably influenced the mobilization of radiostroncium and radiocerium. It is efficient in any case when the radioisotope enters the peritoneal cavity, subcutaneous interstitial tissues, or lungs. Studies on several hundreds of test animals have revealed no detrimental side-effect thus, the composition of this invention is expected to be suitable for curing radioisotope-infected human patients as well.

As it was concluded from the data in Table I, in the earlier studies with cryptate-(2.2.2) ligand for the removal of radiostroncium from living organisms, only the behaviour of metal/ligand complex formed in vitro was investigated when administered into the body (Müller, 1970; Müller et al., 1974 and 1977; Knajfl et al., 1976). Only J. Batsch et al. (Nukleonika 23, 305 /1978/) reported an experimental arrangement in which radiostroncium was ingested intravenously into rats followed by posterior treatment with cryptate-(2.2.2) peritoneally 0.5, 2, 4, 24, 48, 72, 192 and 216 hours later. In order to attain a considerable decorporation, a very high load of the active agent, 10 to 80 mg per animal, was necessary which was equal to or even higher than the semilethal dose ($LD_{50/30}$). It should be mentioned that acute toxicity of cryptate-(2.2.2) for rats in term of $LD_{50}$ is 292 μmole/kg (I.C.R.P. Publication No. 20, p. 76 /1972/). Even in these treatments, the reduction in the retention was never greater than 10 to 12 percent. On the contrary, the composition of this invention reduced radioactivity in rats to 49.6 percent at a load of 1/10 of the semilethal dose (cf. Example 2 and FIG. 6) demonstrating the highly favourable efficiency of the composition of this invention.

What we claim is:

1. A method for decorporating radioactive isotopes of alkaline earth, and rare earth metal compounds from a living organism, which comprises administering to said organism a composition of 1, 4, 10, 13-tetraoxa-7, 16-diazacyclooctadecane-N,N$^1$-dimalonic acid tetrasodium salt, and a pharmaceutically acceptable carrier.

2. The method of claim 1, wherein the composition is administered intravenously.

3. The method of claim 1, wherein the composition is administered intraperitioneally.

4. A pharmaceutical composition for decorporating radioactive metal isotopes of alkaline earth, and rare earth metal compounds from living organisms, comprising 1, 4, 10, 13-tetraoxa-7, 16-diazacyclooctadecane-N, N$^1$-dimalonic acid tetrasodium salt and a pharmaceutically acceptable carrier.

5. The pharmaceutical composition of claim 4 wherein the carrier is a sterilized normal saline solution or a 5-percent by volume of a glucose solution.

6. The pharmaceutical composition of claim 4 wherein 100 to 500 mg of the 1, 4, 10, 13-tetraoxa-7, 16-diazacyclooctadecane-N,N$^1$-dimalonic acid tetrasodium salt is dissolved in 1 cm$^3$ of a 5-percent by volume of glucose solution.

* * * * *